United States Patent [19]

Heppke et al.

[11] Patent Number: 4,874,545
[45] Date of Patent: Oct. 17, 1989

[54] CHIRAL ESTERS OF α-SUBSTITUTED PHENYLALKANOIC ACIDS AND MESOGENIC HYDROXY COMPOUNDS, AND THEIR USE AS A DOPING SUBSTANCE IN LIQUID CRYSTAL PHASES

[75] Inventors: Gerd Heppke; Günter Scherowsky; Christian Bahr; Lutz Lehmann, all of Berlin, Fed. Rep. of Germany

[73] Assignee: Hoechst Aktiengesellschaft, Frankfurt am Main, Fed. Rep. of Germany

[21] Appl. No.: 62,062

[22] Filed: Jun. 12, 1987

[30] Foreign Application Priority Data

Jun. 14, 1986 [DE] Fed. Rep. of Germany ....... 3620049

[51] Int. Cl.$^4$ .................. C09K 19/34; C09K 19/30; C09K 19/20; C09K 19/12
[52] U.S. Cl. .................... 252/299.61; 252/299.01; 252/299.63; 252/299.64; 252/299.65; 252/299.66; 252/299.67; 252/299.68; 252/299.6; 350/350 R; 350/350 S
[58] Field of Search ............ 252/299.01, 299.5, 299.6, 252/299.61, 299.63, 299.65, 299.66, 299.67, 299/68, 299.64; 350/350 R, 350 S; 544/296, 298, 318, 335; 560/18, 59, 60

[56] References Cited

U.S. PATENT DOCUMENTS

| | | | |
|---|---|---|---|
| 4,576,732 | 3/1986 | Isogai et al. | 252/299.65 |
| 4,592,858 | 6/1986 | Higuchi et al. | 252/299.66 |
| 4,613,209 | 9/1986 | Goodby et al. | 350/350 S |
| 4,650,600 | 3/1987 | Heppke et al. | 252/299.01 |
| 4,686,305 | 8/1987 | Sugimori | 252/299.61 |
| 4,695,651 | 9/1987 | Higuchi et al. | 252/299.66 |
| 4,710,585 | 12/1987 | Taguchi et al. | 252/299.67 |
| 4,725,688 | 2/1988 | Taguchi et al. | 252/299.01 |
| 4,728,458 | 3/1988 | Higuchi et al. | 252/299.65 |
| 4,744,918 | 5/1988 | Heppke et al. | 252/299.61 |

FOREIGN PATENT DOCUMENTS

| | | |
|---|---|---|
| 0159872 | 10/1985 | European Pat. Off. |
| 0217240 | 4/1987 | European Pat. Off. |
| 61-174294 | 8/1986 | Japan ............. 252/299.63 |
| WO88/02390 | 4/1988 | World Int. Prop. O. |

OTHER PUBLICATIONS

Molecular Crystals and Liquid Crystals, Gordon and Breach Science Publishers; vol. 148, pp. 29–43 (1987).
Goodby et al., Liquid Crystals & Ordered Fluids, vol. 4, pp. 1–32 (1984).
CA 96:191051g (1982).

Primary Examiner—John F. Terapane
Assistant Examiner—J. E. Thomas
Attorney, Agent, or Firm—Curtis, Morris & Safford

[57] ABSTRACT

The novel compounds are chiral esters of α-substituted phenylalkanoic acids and mesogenic hydroxy compounds, the symbols in the general formula (I)

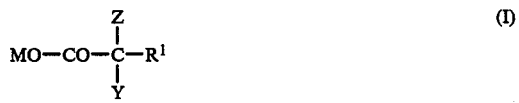

being defined as follows:
MO=molecular radical of a mesogenic hydroxy compound MOH after removal of one H, the radical MO being expressed by the general formula (II)

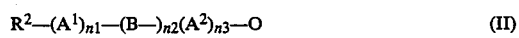

where
$R^2$=straight-chain or branched ($C_1$–$C_{12}$)-alkyl, it being possible for one or two non-adjacent $CH_2$ groups to be replaced by O and/or S atoms, or, if n1=1, also F, Cl, Br, CN or $CF_3$,
$A^1$, $A^2$=independently of one another 1,4-phenylene, diazine-2,5-diyl, diazine-3,6-diyl, 1,4-cyclohexylene, 1,3-dioxane-2,5-diyl, 1,3-dithiane-2,5-diyl or 1,4-bicyclo(2,2,2)octylene, it being possible for these groups also to be at least monosubstituted by F, Cl, Br, CN, $CF_3$ and/or ($C_1$–$C_{12}$)-alkyl (one or two non-adjacent $CH_2$ groups may be replaced by O and/or S atoms),
B=CO—O, O—CO, $CH_2$—$CH_2$, $OCH_2$, $CH_2O$, CH=N, N=CH, N=N, N(O)=N,
n1, n2, n3=independently of one another 0, 1 or 2, n1 and n3 not being 0 simultaneously,
Y=an electron-attracting substituent,
Z=H or an electron-attracting substituent, but not identical with Y, and
$R^1$=benzyl or phenyl, it being possible for these groups to be substituted in the aromatic moiety in the same way as $A^1$ and $A^2$,
with the exception of the compounds with Z=H, Y=F, Cl or Br, $R^2$=($C_1$–$C_{11}$)-alkoxy, $A^1$ and $A^2$=phenyl, $n^1$, and $n^3$=1 and $n^2$=0.

The compounds are preferably used in tilted smectic liquid crystal phases, which are converted into ferroelectric liquid crystal phases by these compounds; they show high values of spontaneous polarization.

3 Claims, No Drawings

CHIRAL ESTERS OF α-SUBSTITUTED PHENYLALKANOIC ACIDS AND MESOGENIC HYDROXY COMPOUNDS, AND THEIR USE AS A DOPING SUBSTANCE IN LIQUID CRYSTAL PHASES

The characteristics of the electro-optical effects used in liquid crystal displays change in general with the temperature. Especially in the case of driving in the multiplexing region, this causes difficulties which can lead to an undesired restriction in the working temperature range. For various electro-optical effects, the temperature dependence of the electro-optical characteristics can be influenced advantageously by an addition of chiral compounds to the nematic liquid crystal, via the temperature function of the pitch of the cholesteric helix structure thus induced, for example for the cholesteric-nematic phase transition effect, the TN (twisted nematic) cell and the recently introduced SBE (supertwisted birefringence effect) and STN (supertwisted nematic) effects.

In addition to nematic and cholesteric liquid crystals, tilted smectic liquid crystal phases have also gained in the last few years an increasing importance for applications in practice. If suitable doping substances, which show a so-called spontaneous polarization ($P_s$), are added to such tilted smectic phases, in particular smectic C ($S_c$ or SmC) phases, the said phases can be converted into a ferroelectric liquid crystal phase (designation of $P_s$ in $nC \times cm^{-2}$); in this connection see, for example, Largerwall et al. in the paper "Ferroelectric Liquid Crystals for Displays", SID Symposium, October meeting, 1985, San Diego (USA).

In EP-A 0,159,872, compounds of the general formula below are described, inter alia, which are said to be suitable as a component in liquid crystal systems and show high values of spontaneous polarization:

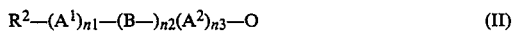

where the substituents should have the following meanings: $R_a = (C_1-C_{18})$-alkyl, X=F, Cl or Br and $R_b$=benzyl or phenyl.

It is the object of the present invention to provide compounds which, at high values of the spontaneous polarization $P_s$, contain structural elements which also render them compatible (i.e. miscible) with other components in liquid crystal systems, since structural elements in the mesogenic part and/or chiral part of the molecules are frequently responsible for good compatibility with the other mixture components in liquid crystal systems.

The invention starts from the known chiral esters of α-substituted phenylalkanoic acids and mesogenic hydroxy compounds. The esters according to the invention are then defined by the symbols in the general formula (I)

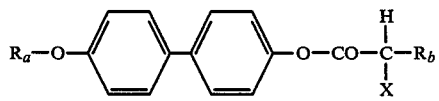

having the following meanings:

MO=molecular radical of a mesogenic hydroxy compound MOH after removal of one H, the radical MO being expressed by the general formula (II)

$$R^2—(A^1)_{n1}—(B—)_{n2}(A^2)_{n3}—O \qquad (II)$$

where $R^2$=straight-chain or branched ($C_1-C_{12}$)-alkyl, it being possible for one or two non-adjacent $CH_2$ groups to be replaced by O and/or S atoms, or, if n1=1, also F, Cl, Br, CN or $CF_3$, $A^1$, $A^2$=independently of one another 1,4-phenylene, diazine-2,5-diyl, diazine-3,6-diyl, 1,4-cyclohexylene, 1,3-dioxane-2,5-diyl, 1,3-dithiane-2,5-diyl or 1,4-bicyclo(2,2,2)octylene, it being impossible for these groups also to be at least monosubstituted by F, Cl, Br, CN, $CF_3$ and/or ($C_1-C_{12}$-alkyl (one or two non-adjacent $CH_2$ groups may be replaced by O and/or S atoms),

B=CO—O, O—CO, $CH_2$—$CH_2$, $OCH_2$, $CH_2O$, CH=N, N=CH, N=N, N(O)=N, n1, n2, n3=independently of one another 0, 1 or 2, n1 and n3 not being 0 simultaneously, Y=an electron-attracting substituent, Z=H or an electron-attracting substituent but not identical with Y, and $R^1$=benzyl or phenyl, it being possible for these groups to be substituted in the aromatic moiety in the same way as $A^1$ and $A^2$, with the exception of the compounds with Z=H, Y=F, Cl or Br, $R^2$=($C_1-C_{11}$)-alkoxy, $A^1$ and $A^2$=phenyl, n1 and n3=1 and n2=0.

The electron-attracting substituents Y are meant especially to include the $CF_3$ and $OCH_3$ group and also halogens such as Cl or Br or the CN group.

The said compounds are chiral α-mono- or di-substituted phenylacetates or phenylpropionates (i.e. substituted in the 2-position of a chiral phenylalkanoic acid) of phenols (or comparable heterocyclic compounds) or cycloalkanols.

The stated object is also achieved by a twistable liquid crystal phase containing at least one chiral compound which comprises, as the chiral compound, at least one compound of the general formula (I). The term "twistable liquid crystal phase" is to be understood as nematic, cholesteric or tilted smectic, in particular SmC, phases.

The twistable liquid crystal phases comprise 2 to 20 and preferably 2 to 15 components, including at least one of the chiral compounds claimed according to the invention. The other constituents are preferably selected from the known compounds showing nematic, cholesteric and/or tilted smectic phases; these include, for example, Schiff bases, biphenyls, terphenyls, phenylcyclohexanes, cyclohexylbiphenyls, pyrimidines, cinnamates, cholesterol esters and variously bridged, terminal-polar polynuclear esters of p-alkylbenzoic acids. In general, the commercially available liquid crystal phases, even before the addition of the chiral compound(s), are mixtures of the most diverse components, of which at least one is mesogenic, i.e. a compound which, in a derivatized form or as a mixture with certain cocomponents, shows a liquid crystal phase [=formation of at least one enantiotropic (clear point>melting point) or monotropic (clear point<melting point) mesophase].

Amongst the compounds of the general formula (I), those are preferred in which the symbols have the following meanings:
R$^2$=straight-chain (C$_4$-C$_{10}$)-alkyl, it being possible for one CH$_2$ group to be replaced by an O or S atom, A$^1$ and A$^2$=independently of one another unsubstituted 1,4-phenylene, 1,4-cyclohexylene or pyrimidine-2,5-diyl, B=CO—O or O—CO, n1=1, n2=0 or 1 and n3=1 or 2, Y=CF$_3$ and Z=OCH$_3$, or Y=OCH$_3$ and Z=H, and R$^1$=unsubstituted phenyl.

The compounds according to the invention are advantageously prepared by reacting mesogenic compounds of the formula (III) or (III')

MOH            (III)

(MO)$_m$Me      (III')

wherein MO is as defined above, Me is an alkaline earth metal or preferably an alkali metal and m=1 (Me=alkali metal) or m=2 (Me=alkaline earth metal), with compounds of the formula (IV)

$$X^f\text{—CO—}\underset{\underset{Y}{|}}{\overset{\overset{Z}{|}}{C}}\text{—R}^1 \quad \text{(IV)}$$

in which X$^f$ is an OH group or halogen, preferably chlorine, and Z and Y are as defined above.

Preferably, mesogenic hydroxy compounds (III) and acid chlorides (IV; X$^f$=Cl) are used for preparing the compounds, the reaction taking place in the presence of acid acceptors such as amines, for example pyridine or triethylamine, or of alkali metal or alkaline earth metal (hydrogen) carbonates, in general at temperatures between −40° C. and +70° C. It is also possible, however, to react the mesogenic hydroxy compound (III) with the carboxylic acid (IV, X$^f$=OH) itself, namely in the presence of Brönstedt or Lewis acids, if appropriate in the presence of dehydrating agents, or with the aid of condensing reagents such as N,N'-carbonyldiimidazole, dicyclohexylcarbodiimide or azodicarboxylate/triphenylphosphine.

Finally, compounds (I) are also obtained by reacting alkali metal or alkaline earth metal salts of the mesogenic hydroxy compound (III') with the carboxylic acid halide (IV, X$^f$=halogen).

The crude product (I) obtained can be purified in a manner known per se, for example by recrystallization or column chromatography.

The liquid crystal phases contain in general 0.01 to 70% by weight, especially 0.05 to 50% by weight, of the compound or compounds according to the invention.

The compounds according to the invention are suitable especially as doping substances for tilted smectic liquid crystal phases, since they convert the latter into ferroelectric liquid crystal phases.

EXAMPLES 1 TO 4

The phenol or cycloalkanol component is dissolved in pyridine, and an equimolar quantity of (−)-2-methoxy-2-trifluoromethyl-2-phenyl-ethanoyl chloride is added dropwise. While excluding moisture, the mixture is then heated for 60 minutes to 65° C. and then stirred for 12 hours at room temperature. Subsequently, the mixture is poured into ice water, acidified with concentrated hydrochloric acid and extracted with ether several times, and the combined ether phases are washed with aqueous NaHCO$_3$ solution. After drying of the ether phases over MgSO$_4$, concentrating to a smaller volume and supersaturating the phases with petroleum ether, the following products crystallize out in a refrigerator:

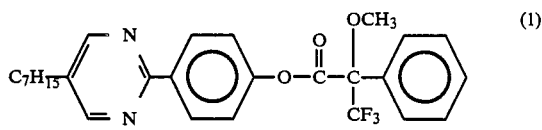

(1)

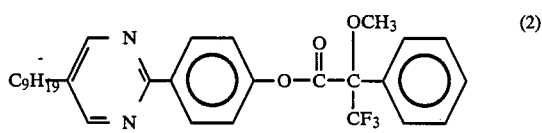

(2)

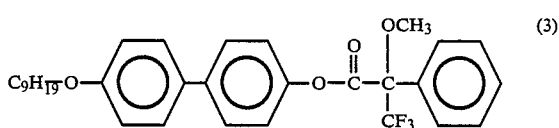

(3)

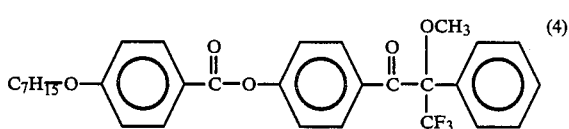

(4)

EXAMPLES 5 AND 6

R-(−)-2-Methoxy-2-phenyl-ethanoic acid in benzene is heated with SOCl$_2$ for 1 hour under reflux and then concentrated in vacuo, and the residue is taken up in absolute benzene. A solution of the phenol or cycloalkanol component in benzene is added and the reaction mixture is treated with pyridine. It is then stirred for 12 hours, poured into water and extracted with ether by shaking, and the organic phase is treated successively with aqueous K$_2$CO$_3$ solution, aqueous saturated NaCl solution, aqueous 3N HCl solution and aqueous saturated NaCl solution. It is then dried (over MgSO$_4$) and concentrated, and the reaction product is purified by column chromatography on silica gel with methylene chloride as the mobile phase.

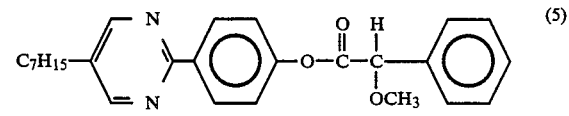

(5)

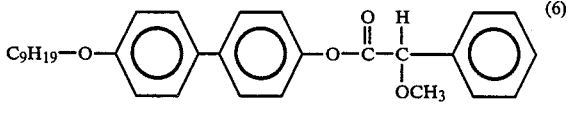

(6)

| Example | Melting point (°C.) | [α]$_D$ in CHCl$_3$ | P$_s$ (nC × cm$^{-2}$)/ at °C. |
|---|---|---|---|
| 1 | 51 | +55° | — |
| 2 | 40.5 | +54° | 5.6/75 |
| 3 | 42 | — | 9.6/76 |
| 4 | 39 | — | 6.6/70 |
| 5 | 35 | −71° | — |

| Example | Melting point (°C.) | $[\alpha]_D$ in CHCl₃ | $P_s$ (nC × cm⁻²)/ at °C. |
|---------|---------------------|------------------------|----------------------------|
| 6 | 68 | −70° | 14.0/70 |

The spontaneous polarization ($P_s$) is determined in the SmC phase of the commercially available compound "HEPTOAB" (manufacturer, for example, Frinton—USA) having the characteristic data "C 74.4 SmC 95.4N 124.2 I", 10 mol% of the particular doping substance being added.

HEPTOAB

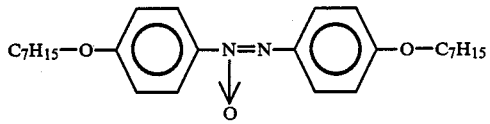

EXAMPLE 7

The compounds according to the invention are also very suitable for inducing a cholesteric helix structure in a nematic liquid crystal phase, in order to exert a positive influence, for example as described at the outset, on the temperature dependence of the electro-optical characteristic of liquid crystal displays.

To determine the twisting capacity, compound (III) was added to a commercially available nematic wide-range mixture—"RO-TN 404" from Hoffmann-La Roche Aktiengesellschaft (Basel/Switzerland)—having a clear point of 104° C.

The values of the twisting capacity in the nematic liquid crystal phase in μm.% by weight (=p.c) are:

| Measuring temperature [°C.] | 10 | 20 | 30 | 40 | 50 | 60 |
|-----------------------------|------|------|------|------|------|------|
| p.c [μm. % by weight] | −12.3 | −12.3 | −12.4 | −12.5 | −12.5 | −12.6 |

We claim:
1. An optically active ester of the formula (I)

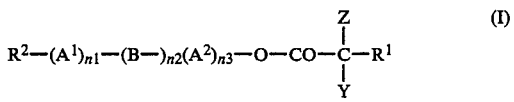

wherein
   R² is a straight-chain (C₄–C₁₀)-alkyl, where one CH₂ group may be replaced by an O or S atom;
   A¹ and A², independently of one another, are 1,4-phenylene, 1,4-cyclohexylene or pyrimidine-2,5-diyl;
   B is CO—O or O—CO;
   n1 is 1;
   n2 is 0 or 1;
   n3 is 1 or 2;
   Y is CF₃;
   Z is OCH₃; and
   R¹ is phenyl.
2. A twistable liquid crystal composition comprising at least two components wherein at least one component is an optically active compound of the formula (I) as claimed in claim 1.
3. A liquid crystal display element containing a liquid crystal composition as claimed in claim 2.

* * * * *